US011287566B2

United States Patent
Matsuba et al.

(10) Patent No.: US 11,287,566 B2
(45) Date of Patent: Mar. 29, 2022

(54) PLASTIC OPTICAL FIBER AND PLASTIC OPTICAL FIBER CORD

(71) Applicant: Toray Industries, Inc., Tokyo (JP)

(72) Inventors: Satoshi Matsuba, Nagoya (JP); Masaaki Umehara, Otsu (JP); Shinji Sato, Nagoya (JP); Hideki Kojima, Nagoya (JP); Yasushi Sawamura, Otsu (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 16/976,115

(22) PCT Filed: Feb. 13, 2019

(86) PCT No.: PCT/JP2019/005070
§ 371 (c)(1),
(2) Date: Aug. 27, 2020

(87) PCT Pub. No.: WO2019/171894
PCT Pub. Date: Sep. 12, 2019

(65) Prior Publication Data
US 2020/0408985 A1  Dec. 31, 2020

(30) Foreign Application Priority Data

Mar. 5, 2018  (JP) .............................. JP2018-038198
Jul. 23, 2018  (JP) .............................. JP2018-137363

(51) Int. Cl.
| | | |
|---|---|---|
| G02B 6/02 | (2006.01) |
| A61B 1/07 | (2006.01) |
| C08F 214/26 | (2006.01) |
| C08L 27/18 | (2006.01) |
| A61B 1/00 | (2006.01) |
| A61F 9/007 | (2006.01) |

(52) U.S. Cl.
CPC ............ *G02B 6/02033* (2013.01); *A61B 1/07* (2013.01); *C08F 214/262* (2013.01); *C08L 27/18* (2013.01); *G02B 6/02395* (2013.01); *A61B 1/0017* (2013.01); *A61F 9/007* (2013.01)

(58) Field of Classification Search
None
See application file for complete search history.

(56) References Cited

U.S. PATENT DOCUMENTS

2006/0127019 A1   6/2006  Castellani et al.
2020/0301064 A1*  9/2020  Kojima .............. G02B 23/2469

FOREIGN PATENT DOCUMENTS

| CN | 102378927 | * | 5/2013 |
|---|---|---|---|
| JP | S43-8978 B | | 4/1968 |
| JP | 61-22305 A | | 1/1986 |
| JP | 63-67164 B2 | | 12/1988 |
| JP | 11-153718 A | | 6/1999 |
| JP | 2003-139971 A | | 5/2003 |
| JP | 2006-195078 A | | 7/2006 |
| JP | 2011-209487 A | | 10/2011 |
| JP | 2011-221450 A | | 11/2011 |
| JP | 2013-041060 A | | 2/2013 |

* cited by examiner

*Primary Examiner* — Chad H Smith
(74) *Attorney, Agent, or Firm* — DLA Piper LLP (US)

(57) ABSTRACT

A plastic optical fiber is excellent in translucency, heat resistance, resistance to environment and the like, and has highly excellent flexibility. The plastic optical fiber contains a core and at least one layer of cladding, wherein the bending elastic modulus of the innermost layer of the cladding is 20 to 70 MPa, the glass transition temperature of the innermost layer of the cladding is 10° C. or lower, and the storage elastic modulus of the innermost layer of the cladding at 30° C. is $1\times10^6$ Pa to $4\times10^7$ Pa.

13 Claims, No Drawings

PLASTIC OPTICAL FIBER AND PLASTIC OPTICAL FIBER CORD

TECHNICAL FIELD

This disclosure relates to a plastic optical fiber that is excellent in translucency, heat resistance, resistance to environment and the like, and also has highly excellent flexibility.

BACKGROUND

Plastic optical fibers are superior to glass optical fibers from the viewpoint of processability, handling property, manufacturing cost and the like and are, therefore, used for short-distance optical signal transmission, light guides, and the like.

In particular, a plastic optical fiber for endoscope lighting used for medical purposes is required to have suppleness and durability to repeated bending for the passage through internal organs having a complicated structure. In addition, in the light guiding sensor for robots and the photoelectric sensor for industrial equipment, the bending driving section is large, which requires excellent flexibility.

A plastic optical fiber is usually made up of two layers of a core and a cladding. For the core, a polymer having excellent transparency and good weather resistance is commonly used, as represented by polymethyl methacrylate (hereinafter abbreviated as PMMA). On the other hand, for the cladding which needs to have a lower refractive index than the core to confine the light inside the core, a fluorine-containing polymer is widely used.

For the plastic optical fiber to have suppleness and durability to repeated bending, it is important that this cladding is flexible, which prevents the cladding from cracking or breaking, and also suppresses an increase in transmission loss caused by irregularities at the interface between the core and the cladding.

Polytetrafluoroethylene (PTFE), which is a typical material for a fluorine-containing polymer, is a material that has suppleness, chemical resistance, and heat resistance, but is problematic for use in plastic optical fibers due to the opaqueness resulted from its crystallinity. Therefore, to ensure transparency, a copolymer in which two or more kinds of fluorine materials are used is usually applied.

As the fluorine-containing polymer for the cladding, the following polymers are widely used in general.
(1) Plastic optical fiber in which a vinylidene fluoride copolymer such as a vinylidene fluoride/tetrafluoroethylene copolymer (JP S63-67164 B) or a vinylidene fluoride/hexafluoroacetone copolymer (JP S61-22305 A) is used as a cladding.
(2) Plastic optical fiber in which a copolymer of fluoroalkyl methacrylate and methyl methacrylate is used as a cladding (JP S43-8978 B).

In applications where suppleness and durability to repeated bending are required, a plastic optical fiber manufactured using these conventional fluorine-containing polymers has caused a problem such as insufficient strength characteristic or worse transmission loss due to the irregularities at the interface.

It could therefore be helpful to provide a plastic optical fiber that is excellent in translucency, heat resistance, resistance to environment and the like, and also has highly excellent flexibility.

SUMMARY

We thus provide a plastic optical fiber comprising a core and at least one layer of cladding, wherein the bending elastic modulus of the innermost layer of the cladding is 20 to 70 MPa. We also provide a plastic optical fiber comprising a core and at least one layer of cladding, wherein the glass transition temperature of the innermost layer of the cladding is −50° C. to 10° C., and the storage elastic modulus of the innermost layer of the cladding at 30° C. is $1 \times 10^6$ Pa to $4 \times 10^7$ Pa.

It is thus possible to provide a plastic optical fiber that is excellent in translucency, heat resistance, resistance to environment and the like, and also has highly excellent flexibility. As a result, a plastic optical fiber having a bending characteristic which is suitable for lighting for medical use as well as for industrial sensor use.

DETAILED DESCRIPTION

Suitable examples of the plastic optical fiber and a plastic optical fiber cord containing the plastic optical fiber will be specifically described below, but this disclosure is not limited to the following examples and can be variously modified and implemented according to the purpose and application.

The plastic optical fiber may comprise a core and at least one layer of cladding, and the bending elastic modulus of the innermost layer of the cladding is 20 to 70 MPa. Furthermore, the plastic optical fiber may be a plastic optical fiber comprising a core and at least one layer of cladding, wherein the glass transition temperature of the innermost layer of the cladding is −50° C. to 10° C., and the storage elastic modulus of the innermost layer of the cladding at 30° C. is $1 \times 10^6$ Pa to $4 \times 10^7$ Pa.

Core

Examples of the polymer (polymer) forming the core include copolymers based on polymethyl methacrylate (PMMA) or methyl methacrylate (for example, copolymers of (meth)acrylic acid esters, (meth)acrylic acid, substituted styrenes, N-substituted maleimides and the like), modified polymers such as glutaric anhydrides and glutarimides obtained by polymerization thereof. A polymer preferably used is a polymer containing methyl methacrylate as a main ingredient, that is, a polymer containing methyl methacrylate in the amount of 50% by mole or more of the repeating units constituting the polymer, preferably 70 mol % or more, and more preferably 90 mol % or more.

Examples of the (meth)acrylic acid esters include methyl acrylate, ethyl methacrylate, butyl methacrylate, t-butyl methacrylate, cyclohexyl methacrylate, benzyl methacrylate, phenyl methacrylate, bornyl methacrylate, adamantyl methacrylate and the like. Examples of the substituted styrenes include styrene, methylstyrene, α-methylstyrene and the like. Examples of N-substituted maleimides include N-isopropylmaleimide, N-cyclohexylmaleimide, N-methylmaleimide, N-ethylmaleimide, N-o-methylphenylmaleimide and the like.

Several of these copolymerizing ingredients may be used, and a small amount of an ingredient other than these may be used as well. In addition, a stabilizer such as an antioxidant may be contained in an amount that does not adversely affect the translucency. Among these polymers, it is most preferred that the polymer is substantially PMMA from the viewpoint of productivity, translucency, resistance to environment, and the like.

Cladding

The bending elastic modulus of the innermost layer of the cladding may be 20 to 70 MPa, the glass transition temperature of the innermost layer of the cladding −50° C. to 10° C., and the storage elastic modulus at 30° C. $1 \times 10^6$ Pa to $4 \times 10^7$ Pa. The innermost layer of the cladding herein refers to the cladding having one layer, or refers to the cladding layer located at the furthest inside when the cladding is formed of several layers.

The "bending elastic modulus of the cladding" as used herein means the bending elastic modulus of the polymer constituting the cladding, and is determined by the method which will be described later. Further, the "glass transition temperature of the cladding" means the glass transition temperature of the polymer constituting the cladding, and the "storage elastic modulus of the cladding at 30° C." means the storage elastic modulus at 30° C. of the polymer constituting the cladding, and these are determined by the method which will be described later. In addition, the polymer includes an aspect of a mixture of polymers and an aspect in which other ingredients are contained (polymer composition), depending on the purpose.

The bending elastic modulus of the innermost layer of the cladding is 20 to 70 MPa, and preferably 20 to 50 MPa. When the bending elastic modulus of the innermost layer of the cladding is less than 20 MPa, the cladding becomes too soft and is easily damaged. When the bending elastic modulus of the innermost layer of the cladding is more than 70 MPa, the cladding becomes hard, which deteriorates the light transmission loss in the bent state.

In general, it is extremely important that a plastic optical fiber used for medical purposes has suppleness and durability to repeated bending because the plastic optical fiber advances and reaches deep inside the body while precisely driving the tip. When the bending elastic modulus of the innermost layer of the cladding is 20 to 70 MPa, these characteristics can be satisfied. The bending elastic modulus herein is a value measured in accordance with ASTM D790. As a typical test piece for ASTM D790, a test piece having a size of 127 mm×13 mm×3.1 mm is used. The unit of measurement for ASTM D790 is kg/cm$^2$, and the bending elastic modulus is calculated from the slope at the point where the slope becomes the largest in the stress-bending displacement curve at the initial stage of stress application, that is, the tangent line at this point.

Moreover, when the plastic optical fiber used for medical purposes is placed inside the body, its temperature gets slightly lower the human body temperature, which is around about 30° C. Therefore, it is important that the plastic optical fiber used for medical purposes has suppleness and durability to repeated bending especially around this temperature. At that time, to secure the adhesion between the cladding and the core materials, it is important that the cladding has rubber elasticity and, therefore, the glass transition temperature of the innermost layer of the cladding is preferably 30° C. or lower, and particularly preferably 20° C. or lower. Further, to prevent the melting point of the cladding from lowering, the glass transition temperature of the innermost layer of the cladding is preferably −50° C. or higher. The glass transition temperature can be measured by using a differential scanning calorimeter (DSC) at a heating rate of 10° C./min according to the method described in JIS K 7121-1987.

The storage elastic modulus of the innermost layer of the cladding at 30° C. is preferably $1 \times 10^6$ Pa to $4 \times 10^7$ Pa from the viewpoint of suppleness, and more preferably $1 \times 10^7$ Pa to $4 \times 10^7$ Pa. By setting the storage elastic modulus at 30° C. to $1 \times 10^6$ Pa or more, it is possible to prevent the conglutination of fibers with each other due to the increased tackiness of the cladding, and it is also possible to improve the processability when the coating layer is coated. By setting the storage elastic modulus at 30° C. to $4 \times 10^7$ Pa or less, the flexibility of the cladding is improved, which prevents the cladding from easily cracking or breaking under bending. Furthermore, irregularities at the interface between the core and the cladding are less likely to occur, and the increase in the transmission loss when the plastic optical fiber is bent is prevented.

To eliminate the influence of the change in the ambient temperature around the plastic optical fiber, the storage elastic modulus of the innermost layer of the cladding at 25° C. to 40° C. is preferably $1 \times 10^6$ Pa to $4 \times 10^7$ Pa, and the storage elastic modulus at 15° C. to 70° C. is more preferably $1 \times 10^6$ Pa to $4 \times 10^7$ Pa.

A cladding layer other than the innermost layer has also preferably the storage elastic modulus in the range described above. That is, the storage elastic modulus of an arbitrary layer of the cladding other than the innermost layer at 30° C. is preferably $1 \times 10^6$ Pa to $4 \times 10^7$ Pa, and more preferably $1 \times 10^7$ Pa to $4 \times 10^7$ Pa. Further, the storage elastic modulus at 25° C. to 40° C. is preferably $1 \times 10^6$ Pa to $4 \times 10^7$ Pa, and the storage elastic modulus at 15° C. to 70° C. is more preferably $1 \times 10^6$ Pa to $4 \times 10^7$ Pa.

The storage elastic modulus is a value measured as follows: a sample of the polymer constituting the layer of the cladding to be measured is heated in a press molding machine at 210° C. for 5 minutes and then cooled to room temperature to mold a test piece having a size of 2.5 cm×0.4 cm and a thickness of 1.4 mm, which is then subjected to a tensile test method described in JIS K 7161-1994, using a dynamic viscoelasticity measuring equipment (DMA).

The plastic optical fiber preferably has a difference of $0.1 \times 10^{-4}$ to $3.0 \times 10^{-4}$ 1° C. in the linear expansion coefficient at 30° C. between the core and the innermost layer of the cladding. In this example, the strain at the interface between the core and the cladding due to a minute temperature change is suppressed, and the adhesion between the core and the cladding is maintained. The linear expansion coefficient is a value measured as follows: a sample of the polymer constituting the layer of the cladding to be measured is heated in a press molding machine at 210° C. for 5 minutes and then cooled to room temperature to mold a test piece having a size of 2.5 cm×0.4 cm and a thickness of 5 mm, which is then measured in a compression mode as described in JIS K 7197-1991, using a thermal analyzing equipment (TMA).

In general, since vinylidene fluoride copolymers have good compatibility with polymers containing methyl methacrylate as a main ingredient such as PMMA, the POF (plastic optical fiber) using vinylidene fluoride copolymers as the cladding has good adhesion at the interface with the core as well as good mechanical characteristics. However, since all of these vinylidene fluoride copolymers are crystalline polymers, the colorless transparency is present only when the composition of the vinylidene fluoride is within a limited range of substantially 70 to 85% by mole. Further, the numerical aperture of the POF of PMMA type in which a vinylidene fluoride copolymer is used as the cladding is around 0.50, and the numerical aperture cannot be increased. Therefore, to obtain a POF having a high numerical aperture, it is necessary to copolymerize a monomer having a higher fluorine content and a lower refractive index.

Therefore, the innermost layer of the cladding is preferably composed of a copolymer containing at least three kinds of ingredients, hexafluoropropylene, tetrafluoroethylene, and vinylidene fluoride as copolymerizing ingredients. The copolymer of vinylidene fluoride and tetrafluoroethylene has high transparency, and the crystallinity can be suppressed when hexafluoropropylene is further contained as an ingredient, and thus suppleness can be imparted. In this way, a flexible plastic optical fiber having a high numerical aperture and excellent translucency can be manufactured.

The content of the vinylidene fluoride in the resin constituting the innermost layer of the cladding is preferably 10 to 35% by weight, more preferably 14 to 30% by weight, and further preferably 14 to 25% by weight. When the content of the vinylidene fluoride is 10% by weight or more, the adhesion at the interface with the core is ameliorated, and the translucency is improved. When the content is 35% by weight or less, the proportion of the fluorine content increases, which decreases the refractive index of the cladding. Thus, a high numerical aperture (also referred to as high NA) is obtained.

The innermost layer of the cladding is preferably composed of a copolymer containing the above-mentioned three fluorine-containing monomers as copolymerizing ingredients. By further adding another fluorine-containing monomer, the copolymer containing four fluorine-containing monomers as copolymerizing ingredients can provide a plastic optical fiber having a high NA and flexibility while maintaining transparency.

The innermost layer of the cladding of the plastic optical fiber may, when the total amount of the monomer ingredients for obtaining the resin constituting the innermost layer of the cladding is 100% by weight, preferably be composed of a copolymer obtained from:

10 to 30% by weight of hexafluoropropylene,
45 to 75% by weight of tetrafluoroethylene,
10 to 35% by weight of vinylidene fluoride, and
1 to 10% by weight of a perfluoroalkylvinylether.

Further, the weight ratio of fluorine constituent is more preferably 70 to 74%. With the composition within this range, it is easy to set the numerical aperture (NA) of the plastic optical fiber to 0.60 to 0.65, and the critical angle at the core/cladding interface is large, which can reduce the loss of the light quantity due to bending. In addition, the adhesion to the core material such as PMMA as a typical example is good. Thus, well-balanced characteristics of the plastic optical fiber that achieve a mechanical characteristic such as flexibility, low tackiness, and heat resistance can be obtained.

The innermost layer of the cladding of the plastic optical fiber may, when the total amount of the monomer ingredients for obtaining the resin constituting the innermost layer of the cladding is 100% by weight, preferably be a copolymer obtained from:

17 to 25% by weight of hexafluoropropylene,
49 to 70% by weight of tetrafluoroethylene,
14 to 30% by weight of vinylidene fluoride, and
2 to 7% by weight of a perfluoroalkylvinylether.

Further, the weight ratio of fluorine constituent of the cladding is more preferably 71 to 74%, and the numerical aperture (NA) of the plastic optical fiber is more preferably 0.61 to 0.65. The NA is further preferably 0.62 to 0.65. More preferably, the NA is 0.62 or more.

Furthermore, the proportion of the weight of hexafluoropropylene with respect to the total weight of tetrafluoroethylene and vinylidene fluoride is preferably 0.250 to 0.360. Since hexafluoropropylene has a trifluoromethyl group in its side chain, hexafluoropropylene has the effect of weakening the intermolecular force between the main chains in copolymer. By setting the proportion of the weight of the hexafluoropropylene to 0.250 or more, flexibility is imparted to the cladding, and thus the adhesion to the core and the strength against bending are improved. Furthermore, by setting the proportion of the hexafluoropropylene to be 0.360 or less, an increase in the tackiness of the cladding and a decrease in the heat resistance due to a lowered melting point can be suppressed. The proportion of the weight of hexafluoropropylene with respect to the total weight of tetrafluoroethylene and vinylidene fluoride is preferably 0.260 to 0.300, and more preferably 0.270 to 0.290. By preferably adjusting the composition of the resin constituting the innermost layer of the cladding as described above, it is easy to achieve the glass transition temperature of the innermost layer of the cladding of 10° C. or lower and the storage elastic modulus at 30° C. of $1 \times 10^6$ Pa to $4 \times 10^7$ Pa.

The melt flow rate (hereinafter, may be abbreviated as MFR) of the innermost layer of the cladding of the plastic optical fiber preferably a value of 10 to 100 g/10 minutes (conditions: temperature of 265° C., load of 5 kg, orifice diameter of 2 mm, length of 8 mm). A particularly preferred MFR is 20 to 60 g/10 minutes. The MFR within the above range facilitates the extrusion, and thus the spinning proceeds smoothly. Further, the adhesion to the core can be appropriately maintained, and the variation of the outer diameter of the plastic optical fiber can be suppressed without decentering.

The innermost layer of the cladding of the plastic optical fiber preferably has a thickness of 2 to 20 μm. A particularly preferred thickness of the cladding is 5 to 12 When the thickness of the cladding is within the above range, the tensile strength as a plastic optical fiber as well as the suppleness are maintained.

Further, at least one layer of cladding can be further provided outside the cladding described above. For the characteristics of the outermost layer of the cladding, it is preferred that the melting point is 150 to 200° C., a refractive index is 1.37 to 1.41, a specific gravity is 1.6 to 1.9, a bending elastic modulus is 1000 to 1500 MPa, and the shear D hardness is 50 to 90. Examples of such a polymer include an ethylene-tetrafluoroethylene copolymer resin in which structural units having a carbonate group are copolymerized. The outermost layer of the cladding is, when the total amount of the monomer ingredients for obtaining the resin constituting the outermost layer of the cladding is 100% by weight, preferably a copolymer obtained from:

10 to 35% by weight of ethylene,
45 to 69% by weight of tetrafluoroethylene, and
20 to 45% by weight of hexafluoropropylene, and 0.01 to 10% by weight of a fluorovinyl compound represented by Formula (1):

$$CH_2=CX^1(CF_2)_nX^2 \qquad (1)$$

wherein $X^1$ represents a fluorine atom or a hydrogen atom, $X^2$ represents a fluorine atom, a hydrogen atom or a carbon atom, and n is an integer of 1 to 10.

More preferably, the outermost layer of the cladding contains a copolymer containing as a copolymerizing ingredient 0.01 to 10% by weight of a fluorovinyl compound represented by $CH_2=CF(CF_2)_3H$.

It is preferred that the outermost layer of the cladding is substantially composed of such a copolymer. The outermost layer of the cladding herein refers to the cladding when the cladding has one layer, or refers to the cladding layer located at the furthest outside when the cladding is formed of two layers or more.

When ethylene is less than 10% by weight in the outermost layer of the cladding, the molding stability is deteriorated in some situations. When ethylene exceeds 35% by weight, the crystallinity is increased, the transparency is decreased and, thus, the transmission characteristic is deteriorated in some situations. The proportion of ethylene is preferably 11 to 30% by weight. When tetrafluoroethylene is less than 45% by weight, the molding stability is deteriorated in some situations. When tetrafluoroethylene exceeds 69% by weight, the crystallinity is increased, the transparency is decreased, and thus, the transmission characteristic is deteriorated in some situations. Further, the melting point is increased, and the fluidity of the optical fiber around the spinning temperature is decreased in some situations. When hexafluoropropylene is less than 20% by weight, the flexibility and bending loss are deteriorated in some situations. When hexafluoropropylene exceeds 45% by weight, the tackiness increases, which in some situations decreases the processability when a coating layer is coated.

In particular, to impart characteristics excellent in adhesion to a (co)polymer of the core containing (methyl) methacrylate as a main ingredient as well as in heat resistance, the fluorovinyl compound represented by Formula (1) is desirably contained in an amount of 0.01 to 10% by weight. From the viewpoint of the relationship with the contents of other copolymerizing ingredients, the content of the fluorovinyl compound is desirably 10% by weight or less.

Further, when the copolymer of the outermost layer of the cladding is a copolymer having a carbonyl group-containing functional group at the polymer chain end or in the side chain, the adhesion with the (co)polymer of the core containing methyl methacrylate as a main ingredient as well as with the coating layer is further improved when the cladding is a single layer, and the adhesion with the coating layer is further improved in an outermost layer of the cladding having two layers or more.

The carbonyl group-containing functional group herein is generally a carbonate group having a —OC(=O)O— bond or a carboxylic acid halide group having a structure of —COY, wherein Y is a halogen element, and particularly preferred examples thereof include a fluorine-containing carbonate (RF—O—C(=O)—RF') or a carboxylic acid fluoride group (—C(=O)F). RF and RF' represent a functional group containing a fluorine group such as a fluorinated alkyl group or a vinylidene fluoride group.

As a protective layer, a vinylidene fluoride (co)polymer such as a vinylidene fluoride/tetrafluoroethylene copolymer, a vinylidene fluoride/hexafluoroacetone copolymer, or vinylidene fluoride homopolymer, or a methmethacrylate-based (co)polymer as in the core, or a polymer such as nylon 12 may be coated further in the thickness of about 2 to 100 μm. This protective layer can be colored by adding a pigment such as carbon black.

The plastic optical fiber can be produced by a general production method. For example, a conjugate spinning method is preferably used, in which a core material and a cladding material in a melting state under heating are discharged from a composite spinneret for a concentric circular conjugate to form a core-sheath two-layer structure of the core/cladding. Subsequently, to improve the mechanical characteristics, a ranging processing by about 1.2 to 3 times is generally performed to obtain a plastic optical fiber. The outer diameter of this plastic optical fiber is usually about 0.1 to 3 mm, and may be appropriately selected according to the purpose, but preferably 0.5 to 1.5 mm from the viewpoint of handling property. In addition, when provided on the protective layer, the plastic optical fiber can be produced by a known method, but a simultaneous conjugate spinning method of three layers is preferably used.

The plastic optical fiber may be further coated by a resin such as polyethylene, polypropylene or copolymers thereof, a blended product, an olefin polymer containing an organic silane group, an ethylene-vinyl acetate copolymer, polyvinyl chloride, polyvinylidene fluoride, a polyamide resin such as nylon 12, a polyester resin, a nylon elastomer, a polyester elastomer or a urethane resin, or a fluorine resin to obtain a cord. The coating layer may be a single layer or multiple layers, and in multiple layers, a tension member such as Kevlar may be inserted therebetween. These coating materials may contain a stabilizer such as an antioxidant, an age-resistor, or a UV stabilizer in addition to a flame retardant. The coating layer can be formed by a known method such as a melt extrusion molding method using a cross head die.

The plastic optical fiber and the plastic optical fiber cord are used suitably for applications in wiring of moving vehicles such as automobiles, aircrafts, ships, and trains, short-distance communication wiring for AV equipment, household equipment, office equipment and the like, lighting for medical endoscopes, lighting for catheters, lighting for microscopes, light guiding sensors for robots, photoelectric sensors for industrial equipment, automobile collision sensors, wall decoration lighting, indoor lighting and the like. In particular, by virtue of the high aperture ratio and appropriate flexibility, and also the property that the transmission loss is unlikely to be reduced even upon bending, the plastic optical fiber and the plastic optical fiber cord are suitable for endoscope, ophthalmic surgery, and catheter applications, and especially suitable for the endoscope application for the usage with thin tissues such as a bile duct and a pancreatic duct.

EXAMPLES

Our fibers and cords will be described below further in detail by way of Examples. The cladding materials and the plastic optical fibers produced were evaluated by the following methods:

Composition ratio: A solid-state $^{19}F$ NMR (AVANCE NEO 400 manufactured by Bruker Corporation) was used for the determination.

Specific gravity: The measuring method of ASTM D792 was used.

Shear D hardness: The measuring method of ASTM D2240 was used.

Bending elastic modulus: The measuring method of ASTM D790 was used. The size of the test piece was 127 mm×13 mm×3.1 mm. The unit of measurement for ASTM D790 was $kg/cm^2$, and the bending elastic modulus was calculated from the slope at the point where the slope became the largest in the stress-bending displacement curve at the initial stage of stress application, that is, the tangent line at this point.

Refractive index: The Abbe's refractometer was used as a measuring equipment, and the measurement was performed in an atmosphere at room temperature of 25° C.

Translucency: A halogen lamp for parallel light (wavelength of 650 nm, incidence NA=0.25) was used for the measurement by a 30/2 m cutting-back method.

Continuous bending number of times up to breaking: A load of 500 g was applied to one end of the fiber; the fiber was supported by a mandrel having a diameter of φ30 mm; the other end of the fiber was continuously bent at an angle of 90° around the supporting point until the fiber broke; the number of times of bending up to the breaking was measured (average value of n=5).

Light transmission loss in a bent state: An LED (light emitting diode) having an emission wavelength of 660 nm was used; the light quantity was measured when the fiber was wound around a metal rod having a radius of 5 mm by 360 degrees; and the decrease amount (before and after) was used as an index.

Light transmission loss after twisting: An LED (light emitting diode) having an emission wavelength of 660 nm was used; both ends of the fiber with a test length of 200 mm were held with clamps and twisted by 180° clockwise and counterclockwise 500,000 times; and the decrease amount of the light quantity (before and after) was used as an index.

Heat resistance: A fiber with a test length of 28 m was put in a high temperature oven (PHH-200 manufactured by Tabai Espec Corp.) at 85° C. for 500 hours (the length of 1 m at each end was outside the oven); the light quantity before and after the test was measured; and the variation amount was used as an index (average value of n=3). The minus indicates that the light quantity decreased).

Storage elastic modulus: The sample was heated at 210° C. for 5 minutes using a press molding machine (IMC-1AE4 manufactured by Imoto machinery Co., LTD), then cooled to room temperature, and molded into a size of 2.5 cm×0.4 cm with a thickness of 1.4 mm; and then the storage elastic modulus at 30° C. was measured by a dynamic viscoelasticity measuring equipment (DVA-200 manufactured by IT Measurement Control Co., Ltd.) in accordance with JIS K 7161-1994.

Glass transition temperature (Tg): A differential scanning calorimeter (DSC) was used for the measurement. The heating rate was 10° C./min. The glass transition temperature was defined as the intersection of a straight line extending from the baseline on the low temperature side to the high temperature side and a tangent line drawn at the point where the gradient of the curve of the step transition portion of the glass transition became maximum.

Linear expansion coefficient: The sample was heated at 210° C. for 5 minutes using a press molding machine (IMC-1AE4 manufactured by Imoto machinery Co., LTD), then cooled to room temperature, and molded into a size of 2.5 cm×0.4 cm with a thickness of 5 mm; and then the linear expansion coefficient was measured by a thermal analyzing equipment (EXSTAR TMA/SS6100 manufactured by Hitachi High-Tech Science Corporation) in accordance with JIS K 7197-1991.

Example 1

As a cladding material, vinylidene fluoride (2F)/tetrafluoroethylene (4F)/hexafluoropropylene (6F)/heptafluoropropyl vinylether copolymer having a copolymerization ratio shown in Table 1 (refractive index of 1.360, fluorine content of 71.7%) was fed to a conjugate spinner. Furthermore, PMMA (refractive index of 1.492) produced by continuous bulk polymerization was supplied as a core material to the conjugate spinner, and the core and the cladding were subjected to core-sheath conjugate melt spinning at 240° C. to obtain a bare fiber having diameter of 1000 μm (core diameter of 980 μm and cladding thickness of 10.0 μm).

The POF thus obtained was evaluated by the evaluation methods as described above, and the results are shown in Table 1. As seen from Table 1, the numerical aperture was high, and translucency, repeated bending characteristic, bending characteristic, twisting characteristic, and heat resistance were excellent and suitable for a plastic optical fiber.

Examples 2 to 4, Comparative Examples 1 to 7

POFs were obtained in the same manner as in Example 1 except that the cladding material was changed as in Table 1. These POFs were evaluated in the same manner as in Example 1, and the results are shown in Table 1.

Examples 2 to 4 were excellent in repeated bending characteristic, light transmission loss upon bending, and light transmission loss upon twisting.

That is, in comparison with Comparative Examples 1 to 6 in which the proportion of the weight of hexafluoropropylene with respect to the total weight of tetrafluoroethylene and vinylidene fluoride was low, Examples 1 to 4 are excellent in the mechanical characteristics, and particularly excellent in light transmission loss upon bending. Further, Comparative Example 7, which was a copolymer of two kinds of fluorine materials, had a low numerical aperture and was inferior in the mechanical characteristics and the heat resistance.

Example 5

POF was obtained in the same manner as in Example 1 except that the cladding material was changed as in Table 1 and that the core/cladding inner layer/cladding outer layer were arranged in a concentric circular manner using a conjugate spinner of the three-layer lamination type. The POF thus obtained was evaluated in the same manner as in Example 1, and the results are shown in Table 1. Compared to Example 1, the continuous bending number of times and the heat resistance were improved.

In Table 1, the fluorovinyl compound is $CH_2$=$CF(CF_2)_3H$.

TABLE 1

| | Core Composition (refractive index) | Composition (wt %) | Inner layer cladding characteristics | | | | | | |
|---|---|---|---|---|---|---|---|---|---|
| | | | Refractive index (numerical aperture) | Bending elastic modulus (MPa) | Fluorine constituent weight (wt %) | 6F/ (2F + 4F) [Weight ratio] | Storage elastic modulus (Pa) | Tg (° C.) | Coefficient of linear expansion (×10$^5$/° C.) |
| Example 1 | PMMA (1.492) | 2F/4F/6F/ heptafluoropropyl vinylether = 19/56/21/4 | 1.351 (0.63) | 31 | 73.1 | 0.280 | 3.5 × 10$^7$ | 7 | 18.4 |
| Example 2 | PMMA (1.492) | 2F/4F/6F/ heptafluoropropyl vinylether = 19/52/25/4 | 1.351 (0.63) | 44 | 73.1 | 0.352 | 8.9 × 10$^6$ | 0 | 20.3 |
| Example 3 | PMMA (1.492) | 2F/4F/6F/ heptafluoropropyl vinylether = 20/55/20/5 | 1.364 (0.60) | 68 | 72.7 | 0.267 | 3.7 × 10$^7$ | 6 | 18.2 |

TABLE 1-continued

| | | | | | | | | | |
|---|---|---|---|---|---|---|---|---|---|
| Example 4 | PMMA (1.492) | 2F/4F/6F = 40/40/20 | 1.364 (0.60) | 57 | 71.5 | 0.250 | $3.8 \times 10^7$ | 5 | 18.4 |
| Example 5 | PMMA (1.492) | Cladding inner layer: 2F/4F/6F/ heptafluoropropyl vinylether = 19/56/21/4 Cladding outer layer: ethylene/4F/6F/ Fluorovinyl compound = 20/54.5/25/0.5 | 1.351 (0.63) | 31 | 73.1 | 0.280 | $3.5 \times 10^7$ | 7 | 18.4 |
| Comparative Example 1 | PMMA (1.492) | 2F/4F/6F/ heptafluoropropyl vinylether = 19/58/19/4 | 1.351 (0.63) | 81 | 72.8 | 0.247 | $7.6 \times 10^7$ | 17 | 17.7 |
| Comparative Example 2 | PMMA (1.492) | 2F/4F/6F/ heptafluoropropyl vinylether = 16/66/16/2 | 1.348 (0.64) | 200 | 73.8 | 0.195 | $8.0 \times 10^7$ | 17 | 17.6 |
| Comparative Example 3 | PMMA (1.492) | 2F/4F/6F/ heptafluoropropyl vinylether = 24/53/19/4 | 1.360 (0.61) | 110 | 72.5 | 0.247 | $4.2 \times 10^7$ | 8 | 17.8 |
| Comparative Example 4 | PMMA (1.492) | 2F/4F/6F/ heptafluoropropyl vinylether = 19/59/19/3 | 1.351 (0.63) | 160 | 73.3 | 0.244 | $4.2 \times 10^7$ | 8 | 17.9 |
| Comparative Example 5 | PMMA (1.492) | 2F/4F/6F/ Trifluoroethylene = 19/59/19/3 | 1.358 (0.62) | 100 | 74.0 | 0.244 | $4.4 \times 10^7$ | 9 | 18.1 |
| Comparative Example 6 | PMMA (1.492) | 2F/4F/6F = 25/60/15 | 1.362 (0.61) | 150 | 73.3 | 0.176 | $6.2 \times 10^7$ | 23 | 17.4 |
| Comparative Example 7 | PMMA (1.492) | 2F/4F = 82/18 | 1.405 (0.50) | 740 | 63.6 | 0.000 | $8.6 \times 10^7$ | −35 | 17.0 |

| | Characteristic evaluation results | | | | |
|---|---|---|---|---|---|
| | Core Composition (refractive index) | Trans- lucency (dB/km) | Number of times of continuous bending | Light transmission loss in bent state (dB) | Light transmission loss after twisting (dB) | Heat resistance (dB) |
| Example 1 | PMMA (1.492) | 130 | 4900 | −0.41 | −0.1 | −0.2 |
| Example 2 | PMMA (1.492) | 138 | 5200 | −0.39 | −0.1 | −0.4 |
| Example 3 | PMMA (1.492) | 135 | 5100 | −0.46 | −0.1 | −0.4 |
| Example 4 | PMMA (1.492) | 128 | 4600 | −0.46 | −0.3 | −1.0 |
| Example 5 | PMMA (1.492) | 130 | 5100 | −0.39 | −0.1 | −0.1 |
| Comparative Example 1 | PMMA (1.492) | 128 | 5100 | −0.68 | −0.1 | −0.2 |
| Comparative Example 2 | PMMA (1.492) | 151 | 4300 | −0.63 | −0.4 | −0.2 |
| Comparative Example 3 | PMMA (1.492) | 131 | 4800 | −0.67 | −0.1 | −0.3 |
| Comparative Example 4 | PMMA (1.492) | 128 | 5100 | −0.68 | −0.1 | −0.2 |
| Comparative Example 5 | PMMA (1.492) | 132 | 4800 | −0.66 | −0.2 | −0.5 |
| Comparative Example 6 | PMMA (1.492) | 895 | 3800 | −1.22 | −0.5 | −1.0 |
| Comparative Example 7 | PMMA (1.492) | 128 | 3300 | −1.50 | −0.4 | −1.4 |

The invention claimed is:

1. A plastic optical fiber comprising a core and at least one layer of cladding, wherein a bending elastic modulus of an innermost layer of said cladding is 20 to 70 MPa, and wherein said cladding comprises a copolymer having a weight ratio of fluorine constituent of 70 to 74% and has a numerical aperture (NA) of 0.60 to 0.65.

2. A plastic optical fiber comprising a core and at least one layer of cladding, wherein a glass transition temperature of innermost layer of said cladding is −50° C. to 20° C., and a storage elastic modulus of innermost layer of said cladding at 30° C. is $1 \times 10^6$ Pa to $4 \times 10^7$ Pa.

3. The plastic optical fiber according to claim 2, wherein a difference in a linear expansion coefficient at 30° C. between said core and innermost layer of said cladding is $0.1 \times 10^{-4}$ to $3.0 \times 10^{-4}/°$ C.

4. The plastic optical fiber according to claim 1, wherein said numerical aperture (NA) is 0.62 to 0.65.

5. The plastic optical fiber according to claim 1, wherein the innermost layer of said cladding contains at least hexafluoropropylene, tetrafluoroethylene, and vinylidene fluoride as copolymerizing ingredients.

6. The plastic optical fiber according to claim 5, wherein the innermost layer of said cladding is composed of a copolymer containing as copolymerizing ingredients:
   17 to 25% by weight of hexafluoropropylene,
   49 to 70% by weight of tetrafluoroethylene,
   14 to 30% by weight of vinylidene fluoride, and
   2 to 7% by weight of a perfluoroalkylvinylether.

7. The plastic optical fiber according to claim 6, wherein the innermost layer of said cladding has a proportion of weight of hexafluoropropylene of 0.250 to 0.360 with respect to the total weight of tetrafluoroethylene and vinylidene fluoride.

8. The plastic optical fiber according to claim 1, further comprising at least one layer of cladding outside said cladding, wherein an outermost layer of the cladding is composed of a copolymer containing as copolymerizing ingredients:
   10 to 35% by weight of ethylene,
   45 to 69% by weight of tetrafluoroethylene, and
   20 to 45% by weight of hexafluoropropylene, and 0.01 to 10% by weight of a fluorovinyl compound represented by Formula (1):

$$CH_2=CX^1(CF_2)_nX^2 \qquad (1)$$

wherein $X^1$ represents a fluorine atom or a hydrogen atom, $X^2$ represents a fluorine atom, a hydrogen atom or a carbon atom, and n is an integer of 1 to 10.

9. The plastic optical fiber according to claim 1, wherein said core is a polymer containing methyl methacrylate as a main ingredient.

10. A medical device comprising the plastic optical fiber according to claim 1.

11. The medical device according to claim 10, wherein said medical device is an endoscope that allows for insertion of an observation probe thereof into a bile duct or a pancreatic duct.

12. A plastic optical fiber cord, comprising at least one coating layer outside the plastic optical fiber according to claim 1.

13. The medical device according to claim 10, comprising a device for ophthalmic surgery or a catheter.

* * * * *